(12) United States Patent
Luzzara

(10) Patent No.: US 8,519,370 B2
(45) Date of Patent: Aug. 27, 2013

(54) MODIFYING RADIATION BEAM SHAPES

(75) Inventor: Marco Luzzara, Crawley (GB)

(73) Assignee: Elekta AB (publ), Stockholm (SE)

( * ) Notice: Subject to any disclaimer, the term of this patent is extended or adjusted under 35 U.S.C. 154(b) by 245 days.

(21) Appl. No.: 13/083,680

(22) Filed: Apr. 11, 2011

(65) Prior Publication Data

US 2012/0256103 A1    Oct. 11, 2012

(51) Int. Cl.
*G21K 5/00* (2006.01)
(52) U.S. Cl.
USPC .................. 250/505.1; 250/492.1; 250/492.3
(58) Field of Classification Search
USPC ..................................................... 250/505.1
See application file for complete search history.

(56) References Cited

U.S. PATENT DOCUMENTS

| | | | |
|---|---|---|---|
| 5,591,983 A | 1/1997 | Yao | |
| 5,757,881 A | 5/1998 | Hughes | |
| 6,459,769 B1 * | 10/2002 | Cosman | 378/147 |
| 6,600,810 B1 | 7/2003 | Hughes | |
| 6,714,627 B1 | 3/2004 | Brown et al. | |
| 7,095,823 B2 | 8/2006 | Topolnjak et al. | |

FOREIGN PATENT DOCUMENTS

JP    2006000220    1/2006

* cited by examiner

*Primary Examiner* — Phillip A Johnston
(74) *Attorney, Agent, or Firm* — Goodwin Procter LLP

(57) ABSTRACT

A patient's lesion is localized for the purpose of administering radiation treatment by obtaining a beam shape representation along one or more beam directions of a radiation treatment device. An image corresponding to the lesion is obtained from each beam direction, and the beam shape and image are fixed to a common coordinate system to facilitate alignment.

20 Claims, 9 Drawing Sheets

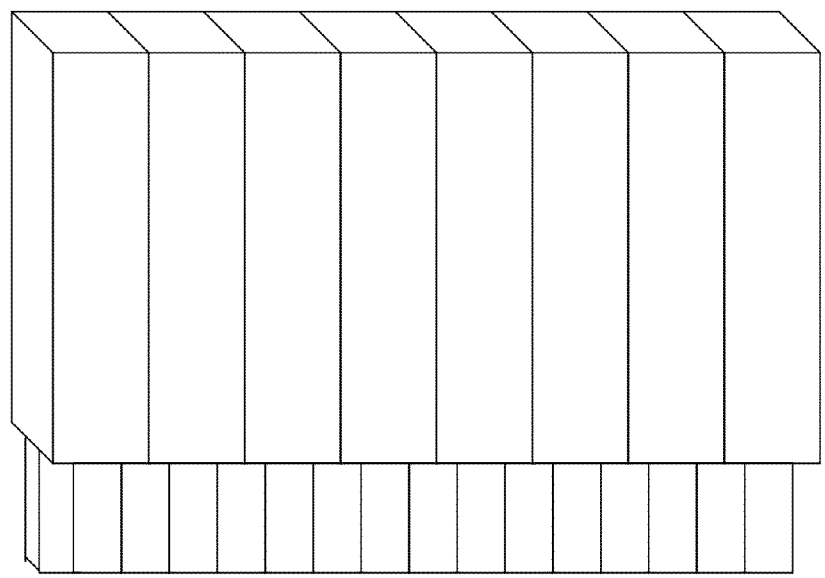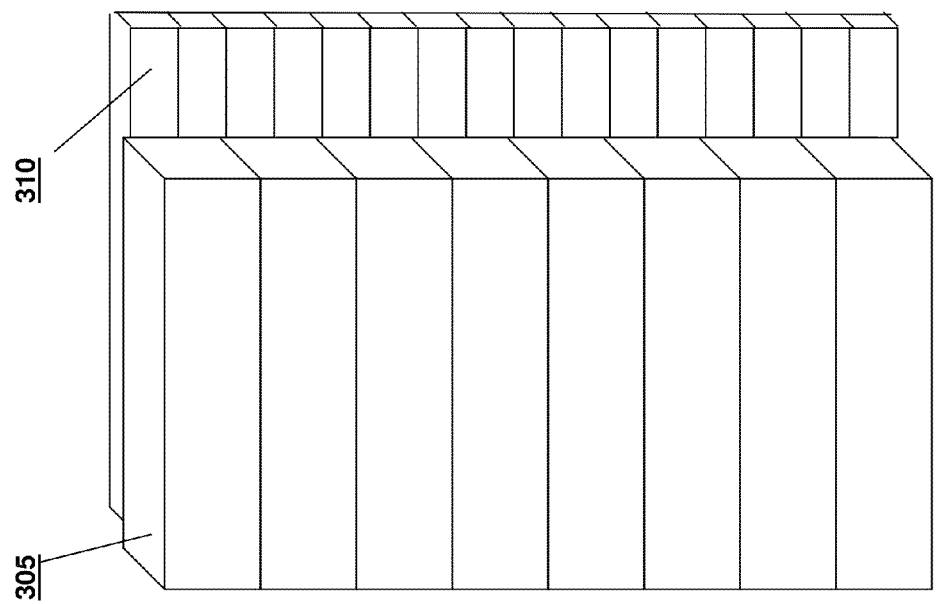
FIG. 3

MODIFYING RADIATION BEAM SHAPES

TECHNICAL FIELD

This invention relates to methods and systems for administering radiotherapy treatments and, more particularly, to methods and apparatus for shaping radiation beams using a multi-leaf collimator.

BACKGROUND INFORMATION

Radiation-emitting devices are used for the treatment of cancerous tumors within patients. The primary goal of treating cancerous tumors with radiation therapy is the eradication of the cancerous cells, while the secondary goal is to avoid, to the maximum possible extent, damaging healthy tissue and organs in the vicinity of the tumor. Typically, a radiation therapy device includes a gantry that can be rotated around a horizontal axis of rotation during the delivery of a therapeutic treatment. A particle linear accelerator ("LINAC") is located within the gantry, and generates a high-energy radiation beam of therapy, such as an electron beam or photon (x-ray) beam. The patient is placed on a treatment table located at the isocenter of the gantry, and the radiation beam is directed towards the tumor or lesion to be treated.

Radiation therapy typically involves a planning stage and a treatment stage. In the planning stage, an X-ray computed tomography (CT) scanner (or similar device) is used to acquire images of a lesion. These images are used to accurately measure the location, size, contour, and number of lesions to be treated in order to establish a dose distribution, and various other irradiation parameters in an attempt to irradiate the lesion while minimizing damage to surrounding healthy tissue.

The advent of 3D conformal radiation therapy (3DCRT) and intensity modulated radiation therapy (IMRT) has improved the ability to minimize this damage. 3DCRT and IMRT use multiple, intersecting, shaped radiation beams, each of which geometrically conforms to the shape of a tumor from the view point of the origin of the radiation beam (the "beam's eye view," or "BEV"). Various types of devices are used to conform the shape of the radiation treatment beam to encompass the tumor along the radiation treatment BEV as it traverses the patient's body into the tumor. One such beam-shielding device is the multi-leaf collimator ("MLC").

LINACs with MLCs facilitate delivery to a patient of radiation beams with arbitrary shapes and distributions. The MLC patterns can be defined during planning, and coupled with 3D conformal treatment planning techniques, they allow treatment plans to be more flexible and complex. Such MLC-based 3DCRT plans prescribe radiation field geometries tailored to fit the tumor's shape more accurately than previous, 2D block-shaped plans. As a result, higher doses can be targeted at the tumor, requiring tighter safety margins around the tumor to avoid damaging healthy tissue by exposing it to the higher, deadlier doses.

Miniature multi-leaf collimators (MMLCs) are also used for finer confirmation of radiation beams. The leaf widths for a miniature multi-leaf collimator are typically thinner than those for a multi-leaf collimator, usually in the range of 2-4 mm. Conventionally, miniature multi-leaf collimators are mounted onto the head of the LINAC just prior to administration of radiotherapy that requires finer confirmation, such as stereotactic radiosurgery or conformal stereotactic radiotherapy. When the treatment is completed, the miniature multi-leaf collimator is then removed from the linear accelerator.

The procedure of mounting and de-mounting a miniature multi-leaf collimator from a LINAC requires additional time and quality assurance checks, and may risk injury to the patient lying on the treatment couch. Further, it may be difficult to use such a collimator to deliver treatments which use combined fields such as miniature multi-leaf conformed fields and larger fields which are shaped by a larger multi-leaf collimator or other radiation shaping devices such as cut blocks, wedges, radiation jaws, and similar devices. In addition, in some clinical applications it is desirable in the treatment of a specific patient at a particular radiation beam angle to use a narrow conformal field, as would be provided by a miniature multi-leaf collimator, and subsequently use a broader field, as would be provided by a multi-leaf collimator.

SUMMARY OF THE INVENTION

The present invention is directed to a fully-integrated, LINAC-mounted multi-leaf collimator (MLC) apparatus that includes multiple banks of adjustable leaves that are sized and arranged such that they can be moved into and out of the general radiation field of the LINAC to provide alternate modes of radiation beam shaping. In general, the MLC banks include a "finer" bank of leaves (referred to herein as the "second MLC" or "secondary MLC") that does not completely block the radiation beam to the same extent as the primary MLC due to their geometry, spacing and arrangement with respect to the primary MLC. For example, although there are no gaps between the leaves of the secondary MLC, the leaves themselves are not deep enough to attenuate enough of the radiation to be considered capable of shielding the patient on their own. As a result, the secondary MLC reduces the radiation intensity in the penumbra of the beam after it has passed through the first MLC, but crucially, can be much shorter/less deep, and therefore take up less space in the LINAC head, maintaining sufficient clearance with respect to the patient, and reducing the amount of extra weight added to the head.

Therefore, in one aspect, a multi-leaf collimator assembly includes a primary and secondary multi-leaf collimator. The primary MLC includes multiple leaves, each leaf having a first depth and movable relative to a source of radiation, thereby defining an aperture through which the radiation passes and creating a first radiation beam field. The secondary MLC also includes having multiple leaves. At least one of the leaves of the secondary MLC extends into the aperture, and each leaf has a second depth (e.g., between 20 and 40 mm as measured along the direction of the radiation beam) sufficient to partially block a portion of the first radiation beam field, thereby defining a second radiation beam field. The second radiation beam field includes a first subfield and a second subfield (which may include the penumbra of the first beam field) having lower intensity than the first subfield.

In some embodiments, the secondary MLC is positioned apart from and is movable relative to the first multi-leaf collimator. The secondary MLC may be positioned below the primary MLC relative to the source of radiation, or, in some cases, inside the primary MLC. Either or both of the MLCs may be permanently mounted to the source of radiation, such as a LINAC, whereas in other cases the two MLCs are removably mounted to a LINAC as a single unit. In certain arrangements, each leaf of the primary MLC has a first thickness when measured perpendicular to an axis from the source of radiation to a treatment table, and wherein each leaf of the secondary MLC has a second thickness, the second thickness being no greater than half the first thickness. The apparatus may also include a controller for controlling movement of at least one leaf within the primary MLC and two or more leaves of the secondary MLC such that the at least one leaf and the two or more leaves move in concert along a common axis.

In other aspect, a linear accelerator system for applying radiation treatment includes a linear accelerator for generating a radiation beam and a primary and secondary MLC. The primary MLC includes multiple leaves, each leaf having a first depth and movable relative to the linear accelerator, thereby defining an aperture through which the radiation beam passes, and creating a first radiation beam field. The secondary MLC also includes multiple leaves, wherein at least one of the leaves extends into the aperture. Each leaf of the secondary MLC has a second depth sufficient to partially block only a portion of the first radiation beam field, thereby defining a second radiation beam field. The second radiation beam field includes a first subfield and a second subfield, the second subfield having lower intensity than the first subfield.

In a third aspect, a method of delivering radiation therapy includes defining a treatment beam aperture by adjusting the positioning of one or more leaves of a primary MLC. Each leaf of the primary MLC is of a depth sufficient to completely block radiation directed at the primary MLC. A leaf of a secondary MLC is extended into the aperture, where the secondary MLC also has multiple leaves, each leaf being of sufficient depth to partially but not completely block a portion of the first radiation beam field. Radiation therapy is then administered through the aperture.

The method may also include adjusting the positioning of the leaves of the primary MLC, causing the leaf of the second multi-leaf collimator to move in concert with the leaves of the primary MLC. In some arrangements, an end of one leaf of the secondary MLC is aligned with an end of the primary MLC and partially defining the aperture, and a second leaf of the secondary MLC extends beyond the end of the primary MLC into the aperture.

The foregoing and other objects, features and advantages of the present invention disclosed herein, as well as the invention itself, will be more fully understood from the following description of preferred embodiments and claims, when read together with the accompanying drawings. In the drawings, like reference characters generally refer to the same parts throughout the different views. The drawings are not necessarily to scale, emphasis instead generally being placed upon illustrating the principles of the invention.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 3 is an elevation of an MLC assembly used in an embodiment of the invention.

DETAILED DESCRIPTION

Figure 1:
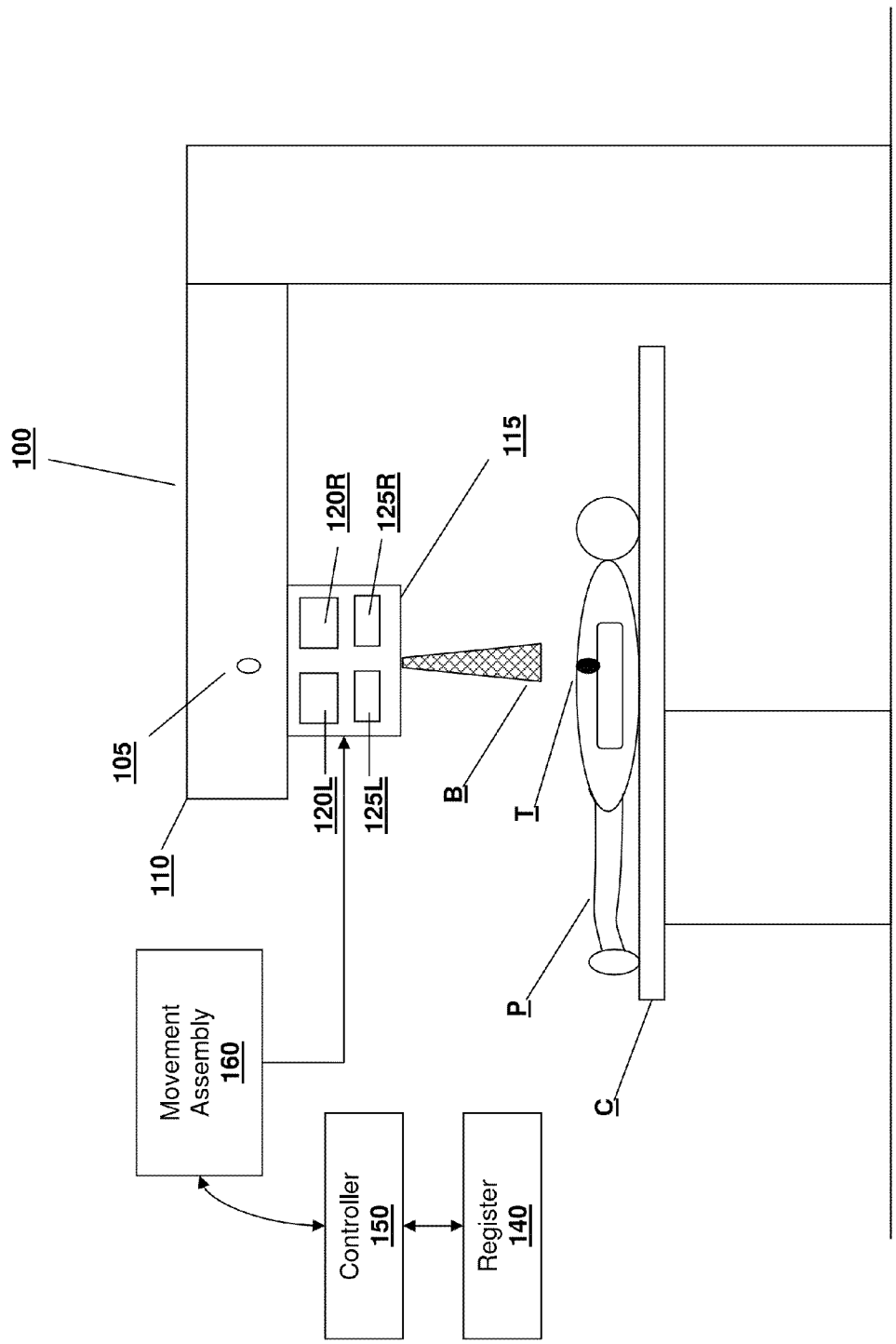
FIG. 1 is a diagrammatic illustration of a LINAC including various features and embodiments of the invention.

Referring to FIG. 1, one embodiment of an apparatus and system in accordance with various embodiments of the invention is shown. A linear accelerator (LINAC) 100 is used to generate and deliver a radiation beam B to a patient P supported on couch C. Typically, the beam B is generated by a radiation source 105 contained within the LINAC head 110. A target volume T has previously been identified and defined in or on the patient's body, to which the beam B is to be administered. The volume T may, for example, be a cancerous tumor which is to be treated by introducing the biological effects of the radiation beam from source 105 to the target T according to a radiation treatment and dosage plan.

Figure 2:
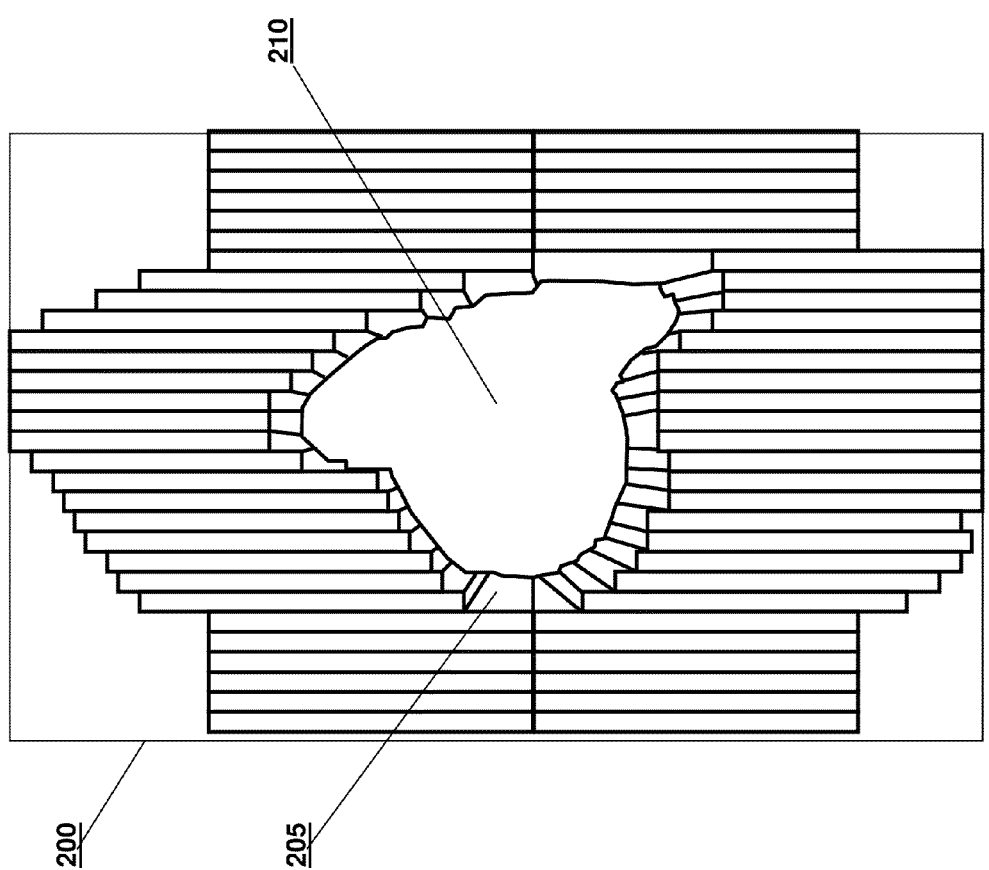
FIG. 2 is an elevation of an MLC assembly used in an embodiment of the invention.

In order to shape, direct and otherwise control the delivery of the radiation beam B to the patient P, a beam-shielding device such as a multi-leaf collimator (MLC) assembly 115 is attached to or contained within the LINAC head 110 to define a radiation field. Referring to FIG. 1, a beam-shielding device is provided in the path of each beam. One example of an MLC includes a plurality of opposing plates or leaves mounted between the radiation source and patient. The leaves can vary in width, length, or thickness, and are substantially impervious to the emitted radiation. Adjusting the leaves blocks the radiation according to the leaf pattern, thus shielding healthy tissue from the radiation being applied to the tumor. The leaves are generally movable in a direction generally perpendicular to the beam as to allow for changes in the size and shape of an irradiation field. This permits an essentially arbitrary shaped beam that can better conform to the size and shape of the lesion, tumor, or structure being treated. Within the thus-shaped beam, the energy of the beam is typically uniform. FIG. 2 illustrates how a conventional MLC apparatus 200 includes multiple leaves 205 which can be moved to create a shaped aperture 210. Because the MLC shields or otherwise deflects the energy from the LINAC, the shaped aperture 210 facilitates the delivery of radiotherapy treatment according to a desired beam shape that coincides with the area, lesion or organ being treated.

Referring again to FIG. 1, MLC assemblies according to various implementations of the present invention include two "banks" of leaves (illustrated as elements 120R and 120L), one bank being positioned on each side of the path of the radiation emanating from the beam source 110 to the patient P. Each bank 120 typically includes multiple tungsten leaves (usually having a width of approximately 1 cm) that move independently of each other along an axis perpendicular to the beam direction to form a beam shape. As the width and composition of the leaves are such that the radiation beam cannot pass through the leaves, adjusting the position of individual leaves of each bank such that the leaves are in the path of the beam B defines the contour or shape of the radiation beam profile as delivered to the patient P.

In addition to the first MLC 120, and according to various embodiments of the invention, a second MLC (illustrated as elements 125R and 125L) may also be attached to, integrated with or otherwise part of the LINAC head 105. The second MLC also has two banks of leaves, albeit smaller in width and depth than the first MLC 120. Each bank of the second MLC 125 may also include multiple tungsten leaves which move independently of each other to further define, influence or alter the beam shape. In such cases, the leaves of the secondary MLC are narrower than those of the first MLC. For example, in implementations in which the leaves of the primary MLC may be 1 cm in width (as measured orthogonal to the direction of the radiation beam as it travels from the source to the target), the leaves of the secondary MLC may be between 2.5 mm and 5 mm. In some cases, maintaining a set ratio (e.g., 2:1) of primary MLC leaf width to secondary MLC leaf width is preferred to reduce the likelihood of radiation leakage.

FIG. 1 also illustrates certain data and image processing components that are used to control the LINAC, the MLCs and the administration of radiation therapy. The components include a register 140, a controller 150 and a movement assembly 160. The register 140, which may be any known organized data storage facility (e.g., partitions in RAM, etc.) may receive images from an imager (not shown) such as an MRI, CT/PET scanner, ultrasound device, or x-ray device. In some embodiments, the images can be stored on a data storage device separate from the imager (e.g., a database, microfiche, etc.) and sent to the register 140. The register 140 may also store treatment parameters for the LINAC and collimator systems and other data used to determine the proper beam shape and radiation dosage. The register 140 may receive the images and beam shapes through conventional data ports and may also include circuitry for receiving analog image data, and analog-to-digital conversion circuitry for digitizing the image data.

The register 140 provides treatment, image and or beam shape data to a controller 150. The controller 150 controls the movement of each of the tungsten leaves within each of the leaf banks 120 and 125, the switching of the beam source 105 on and off, the control beam dose rates, and the control of the position of the LINAC head 110. In certain implementations, the controller 150 includes one or more processors which either programmatically, or in response to instructions from a user, determine the proper leaf positioning to cause the desired beam shape such that the target lesion is substantially encompassed in the beam shape, or, in the case of multiple beam shapes defining an intersection volume, such that the lesion is substantially encompassed by the intersection volume from multiple beam directions. For example, the processor calculates a set of leaf displacements needed for proper beam shapes, which are used by the controller 150 to generate instructions representing physical movements of the MLC leaves. The instructions may, in some cases, be provided to a movement assembly 160 that implement the instructions. Translation and movement of the primary MLC, secondary MLC and/or the dual-MLC assembly as an entire unit may be accomplished using, for example, a series of motors, actuators, gear systems, and lead screws which operate in response to instructions from the controller 150. The movable MLC assembly may be translated on the radiation head of the LINAC itself. In such cases, the entire assembly rotates together with the LINAC collimator head assembly in a way similar to that of a conventional wedge or block trays. The controller and movement assembly may be co-located with the LINAC, located nearby in a separate control room or operating station, or remotely at another location. The controller may include graphical control screens and menu-driven user interfaces to indicate the position and movement of the MLC assembly. As a result, a beam shape is created that addresses the treatment lesion while minimizing radiation that is delivered outside the lesion.

In some embodiments, the register 140 and controller 150 may implement the functionality of the present invention in hardware or software, or a combination of both on a general-purpose computer. In addition, such a program may set aside portions of a computer's random access memory to provide control logic that affects one or more of the image manipulation, fusion, alignment, and support device control. In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software could be implemented in an assembly language directed to a microprocessor resident on a computer. For example, the software can be implemented in Intel 80×86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

Figure 4:
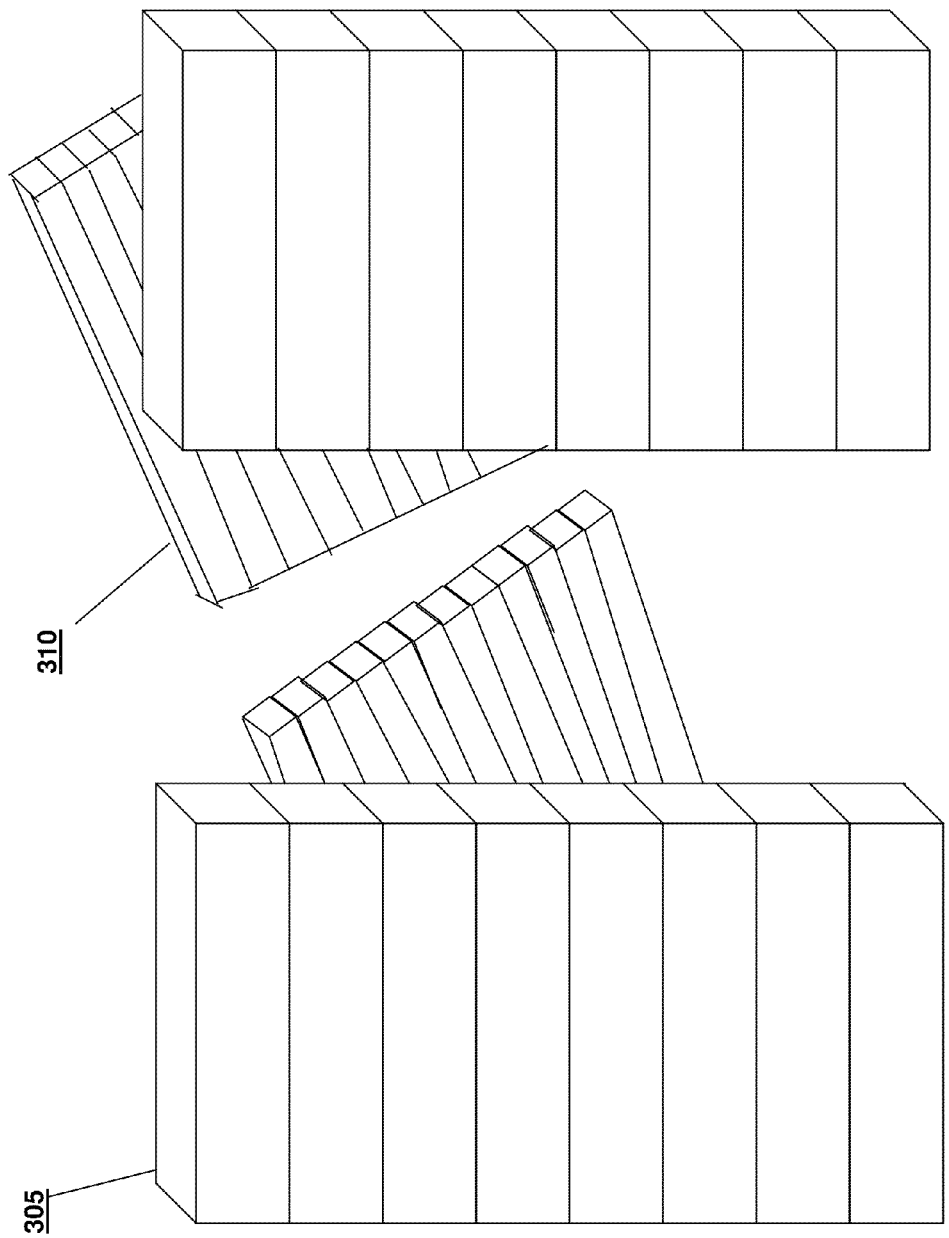
FIG. 4 is an elevation of a rotatable MLC assembly used in an embodiment of the invention.

FIG. 3 illustrates one implementation of a dual MLC arrangement that includes both a first MLC 305 and a second MLC 310. In some cases, the two MLCs are independently mounted within the LINAC head such that one or both may be removed independently of each other. In other implementations, the first MLC 305 and second MLC 310 are fixedly mounted to each other such that removal of both MLCs may be done together. In some instances, multiple (e.g., 2 or more) leaves from the second MLC 310 may be attached to a corresponding leaf of the first MLC 305. In such cases, movement of one leaf of the first MLC 305 inwards or outwards relative to the aperture causes a corresponding movement to multiple leaves of the second MLC 210. The movement may be equivalent (e.g., a shift of the leaf inwards by 3 cm causes each of the corresponding leaves to also shift 3 cm inward) or proportional (e.g, a movement of a leaf of the first MCL 305 by 1 cm causes a movement of 0.5 cm in the corresponding leaves of the second MLC 301). Referring to FIG. 4, in some instances the second MLC 310 may be rotatably connected to the first MLC 305 such that the leaves of each MLC may be arranged in angular fashion relative to each other.

To reduce the amount of space needed to house the two MLCs within the LINAC head, the second, finer MLC leaves are designed such that they are incapable of completely blocking the radiation beam to the same extent as the primary MLC. Therefore, while there may be no gaps between the leaves, the leaves themselves are not be deep enough to attenuate enough of the radiation to be considered capable of shielding the patient on their own. Instead, the second MLC is used in tandem with the first MLC leaf bank which, on its own, can completely block the radiation beam. For example, the secondary MLC having the finer leaves may only be capable of blocking 50% of the intensity of the beam. As such, the smaller MLC is still useful for reducing the intensity of the penumbra of the beam after it has passed through the first MLC, but crucially, can be much shorter/less deep, and therefore take up less space in the LINAC head, maintaining our good patient clearance distance, and reducing the amount of extra weight added to the head.

Figure 5:
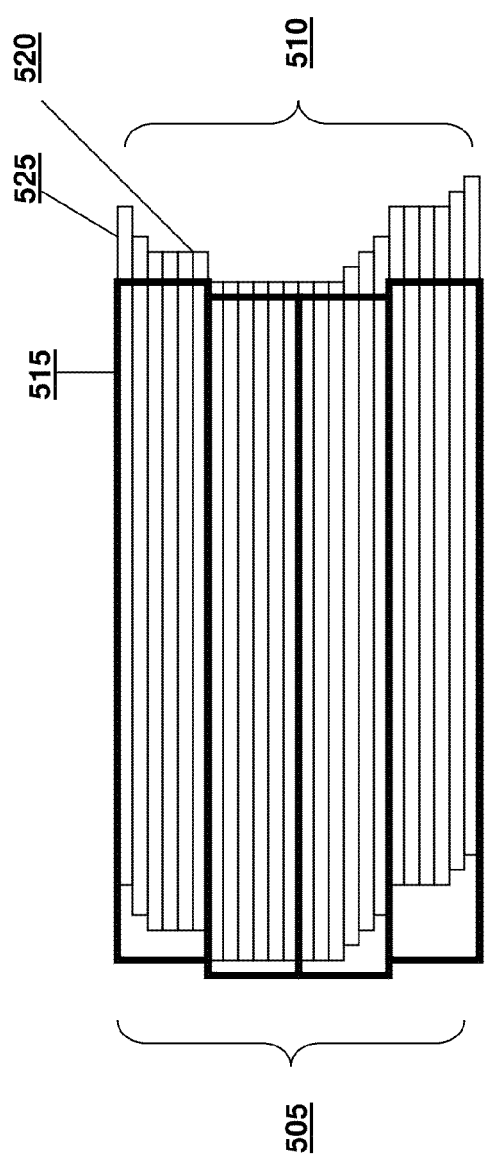
FIG. 5 is an illustration of an dual MLC assembly used in various embodiments of the invention.

FIG. 5. illustrates a view of the dual MLC assembly as seen from the radiation source. Closest to the source are the wider, deeper leaves of the primary MLC 505. Beneath that are shown the outlines of the finer, smaller secondary MLC leaves 510. The distance between the tips of the two banks of leaves has been exaggerated for the purposes of this illustration, but in general, the tip of the primary collimator leaves 505 would align with the tip (or tips) of the most retracted finer leaves 510 of the secondary MLC leaf pair directly below it. In this case, leaf 515 may be positioned so its tip coincides with the tip of leaf 520, leaving leaf 525 extended further out into the aperture. In other cases, the tips of each leaf of the secondary MLC may extend beyond the tip of the corresponding leaves of the primary MLC.

In certain implementations, the two MLC leaf banks are aligned such that they both move along the same axis, and in some cases the MLC leaves of the first bank (the wider leaves) track the motion of the MLC leaves of the second bank (the finer leaves). In such cases, the wider leaves of the first MLC are matched in position to the finer leaves of the second MLC, so that two fine leaves in the second MLC cover the same area at isocentre as the wider leaf in the first MLC. In this case, the movement of the wider leaf is matched to that of the two finer leaves so that the wider leaf is only as far advanced into the beam as the closest of the two leaves it is tracking.

Figure 6:
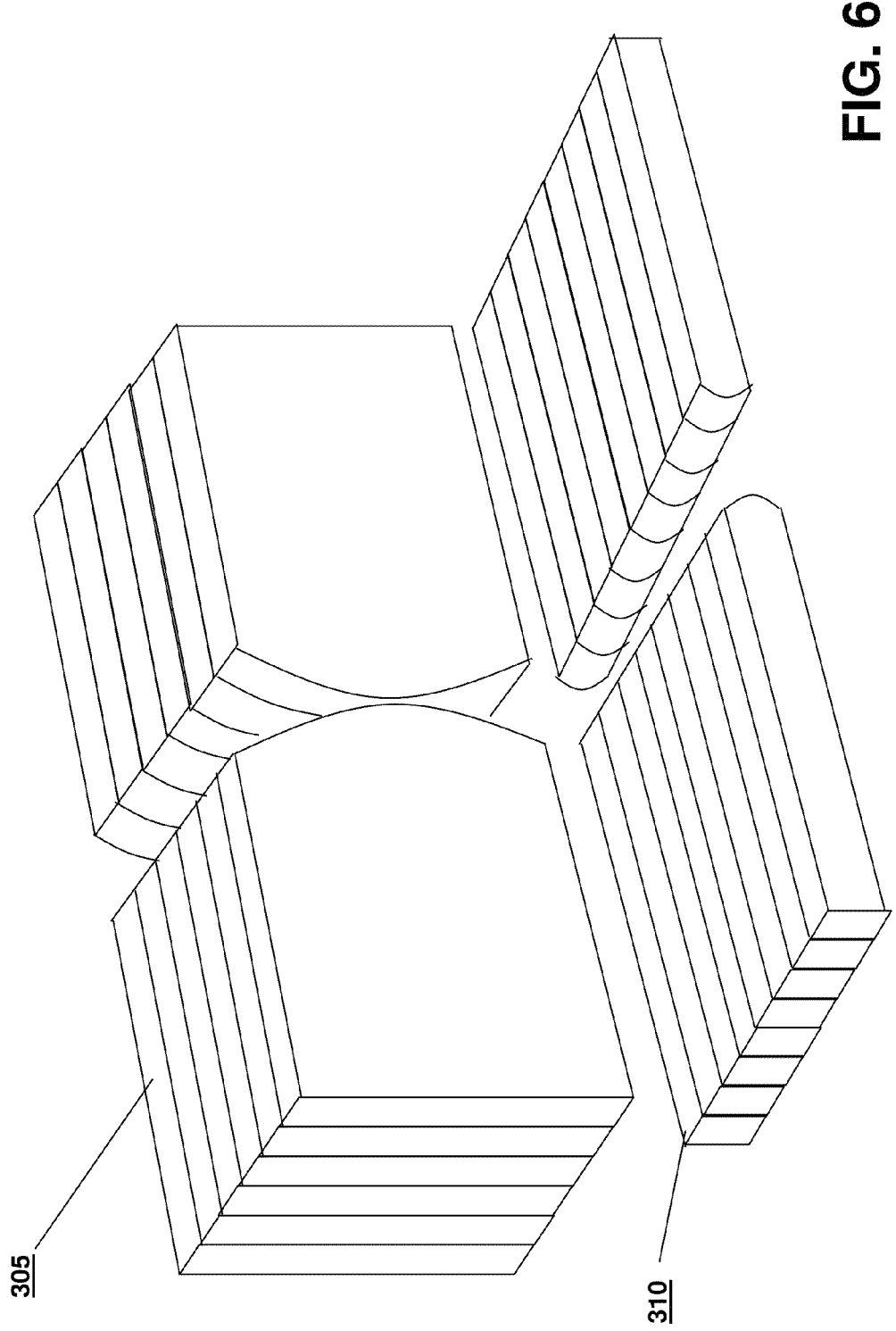
FIG. 6 is a perspective of an MLC assembly according to various embodiments of the invention.

FIG. 6 illustrates a perspective view of the MLC assembly that includes the dual MLC arrangement and illustrates exemplary differences in the sizes of the leaves of the two MLCs. As described above, both the first MLC 305 and second MLC 310 include multiple leaves, however the leaves of the second MLC are smaller in both depth (as measured in the direction along which the beam passes the MLCs) and width (as measured in a direction perpendicular to the direction along which the beam passes). The smaller size allows some (but not all) radiation energy to pass through the secondary MLC, whereas the larger primary MLC blocks all radiation directed towards it. For example, implementations in which the leaves of the primary MLC have a depth of are between 6 cm and 9 cm, the leaves of the second MLC are between 20 mm and 40 mm deep.

Figure 7:
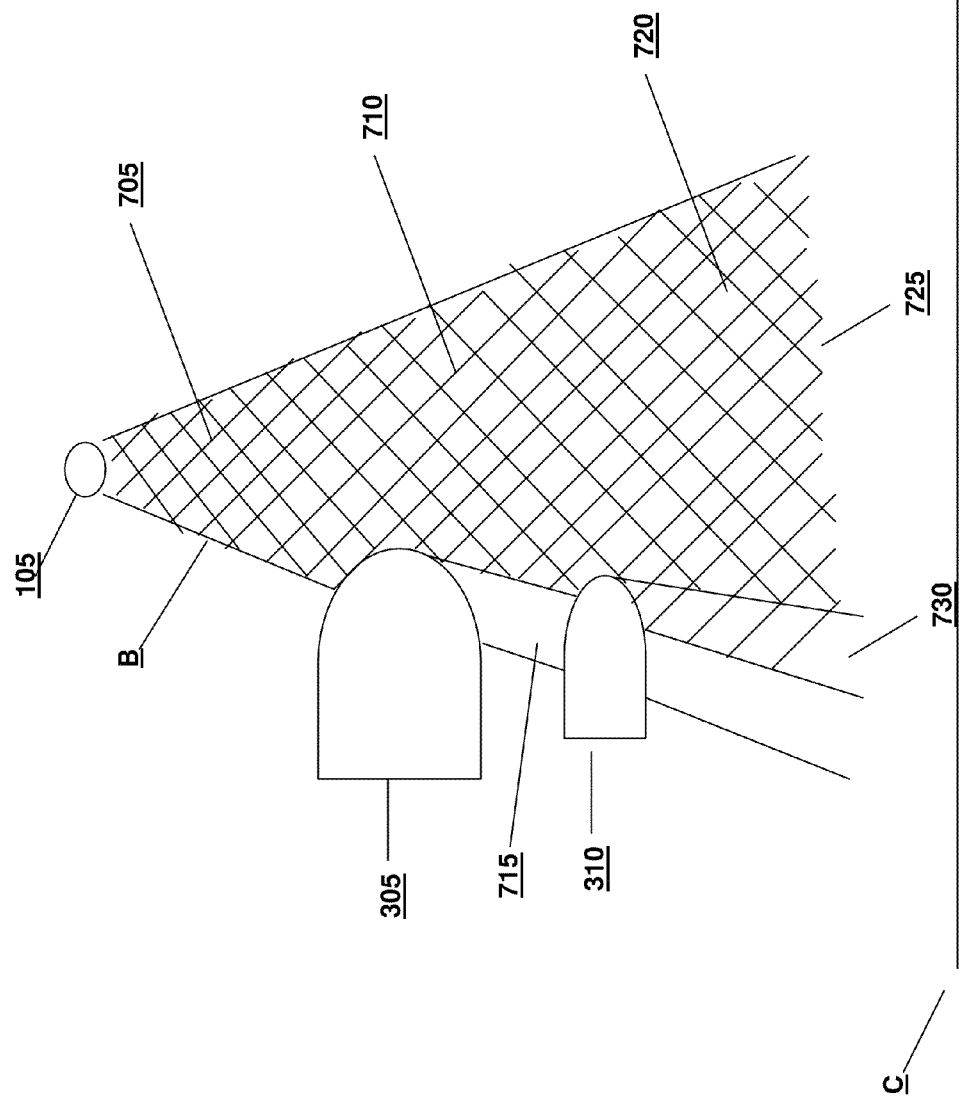
FIG. 7 is an illustration of a radiation beam being affected by an MLC assembly according to various embodiments of the invention.

FIG. 7 illustrates how the dual MLC assembly affects the radiation beam B as delivered from the beam source 105 to the target. The beam shape expands outward as it is projected toward the target from the beam source 105, creating an unaffected radiation beam field 705. As the beam reaches the primary MLC 305, the arrangement of the primary MLC leaves defines an aperture through which the radiation passes, thereby creating a first radiation beam field 710, which essentially comprises the initial, unaffected radiation beam field but excluding the umbra 715. Individual leaves of the secondary MLC 310, being of lesser depth, may extend further into the aperture and affect the first radiation beam field 710 thereby defining a second radiation beam field 720. Because the leaves of are lesser depth and do not completely occlude or deflect the radiation of the first beam field 710, the second beam field 720 includes two subfields, subfield 725 and subfield 730. While the secondary MLC has no effect on subfield 725, it may be capable of blocking 50% of the intensity of the beam, and therefore reduces the intensity of the penumbra 730 of the beam after it has passed through the primary MLC.

Figure 8:
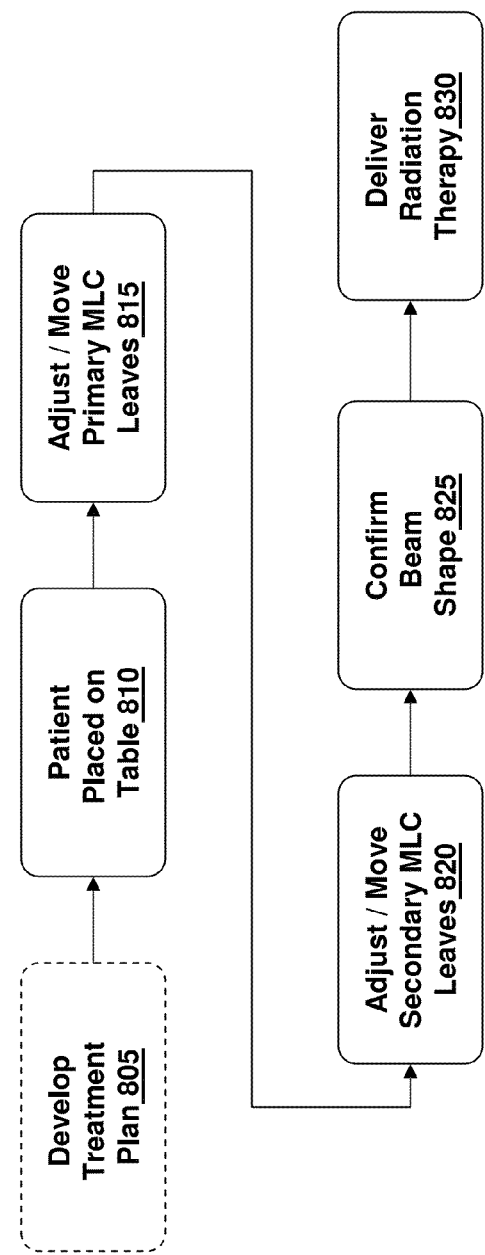
FIG. 8 is a flow chart illustrating steps of a method of using the MLC assembly according to various embodiments of the invention.

FIG. 8 illustrates the operation of a system and implementation of method in accordance with various embodiments of the present invention. Initially (and in some cases optionally) a treatment plan may be developed (STEP 805) based on image scan data based on various imaging modalities to define target volumes and beam positions and shapes. At treatment time, the patient is placed on the radiation delivery machine couch (STEP 810) and prepared for treatment administration. Based on the treatment plan, the primary MLC leaves are moved into the beam field position (STEP 815) and thus shape of the first radiation beam field. The position of the secondary MLC leaves are then adjusted (STEP 820) to further define the treatment beam, creating a second radiation beam field. Once the correct beam shape is confirmed (STEP 825) and the LINAC gantry couch and gantry angles are set according to plan, the radiation beam is delivered from the radiation source through the collimator aperture of the dual MLC assembly to the target (STEP 830). This sequence of steps illustrates a process by which radiation may be delivered to a patient with using a dual MLC assembly that allows different configurations of beam shapes to deliver varied radiation patterns according to clinical needs and in accordance with the present invention.

Figure 9:
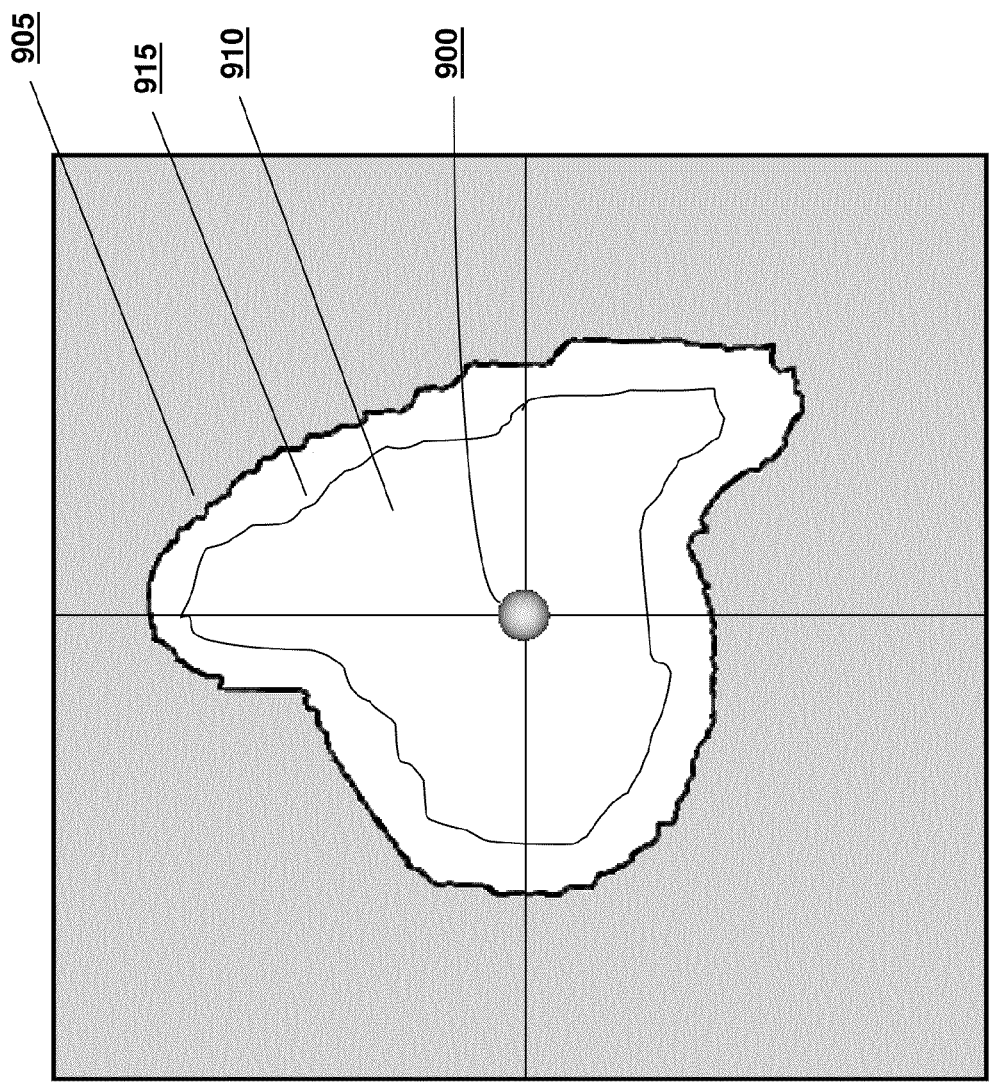
FIG. 9 illustrates a beam shape as administered to a patient according to various embodiments of the invention.

Referring to FIG. 9, the results of using the techniques and systems described above are illustrated as a beam's-eye-view of the radiation beam field in which the isocenter 900 of the radiation beam is aligned with the center (or near the center) of the target to be treated. The alignment of the leaves within the primary multi-leaf collimator are adjusted according to a treatment plan or other guide, thereby defining the initial aperture through which the radiation passes and creates a first radiation beam field 905. The smaller, shallower leaves of the second MLC are further adjusted into the aperture, thereby defining a second radiation beam field that includes two subfields, 910 and 915. The first subfield 910 is the area to which the radiation is being delivered without interference from any MLCs, whereas the second subfield 915 is the area receiving partially-blocked radiation energy as influenced by the second MLC. In some instances, the second subfield may define and/or include the penumbra of the first beam field.

While the invention has been particularly shown and described with reference to specific embodiments, it should be understood by those skilled in the area that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A multi-leaf collimator assembly, the assembly comprising:
   a first multi-leaf collimator having multiple leaves movable relative to a source of radiation and defining an aperture through which a first radiation beam field passes, the leaves of the first multi-leaf collimator having a first depth along a radiation beam direction;
   a second multi-leaf collimator having multiple leaves movable relative to the source of radiation, the leaves of the second multi-leaf collimator having a second depth along the radiation beam direction, the second depth being less than the first depth and insufficient to fully attenuate the first radiation beam field, wherein at least one leaf of the second multi-leaf collimator intersects a portion of the first radiation beam field to define a second radiation beam field comprising a first subfield and a second subfield, the second subfield resulting from the intersection of the at least one leaf of the second multi-leaf collimator with the first radiation beam field and having lower intensity than the first subfield.

2. The multi-leaf collimator assembly of claim 1 wherein the second multi-leaf collimator is positioned apart from and is movable relative to the first multi-leaf collimator.

3. The multi-leaf collimator assembly of claim 2 wherein the second multi-leaf collimator is rotatably movable relative to the first multi-leaf collimator.

4. The multi-leaf collimator assembly of claim 2 wherein the second depth is between 20 millimeters and 40 millimeters.

5. The multi-leaf collimator assembly of claim 2 wherein the second multi-leaf collimator is positioned below the first multi-leaf collimator relative to the source of radiation.

6. The multi-leaf collimator assembly of claim 1 wherein each leaf of the first multi-leaf collimator has a first thickness when measured in a direction perpendicular to an axis from the source of radiation to a treatment table, and wherein each leaf of the second multi-leaf collimator has a second thickness, the second thickness being no greater than half the first thickness.

7. The multi-leaf collimator assembly of claim 1 wherein the second subfield comprises a penumbra of the first radiation beam field.

8. The multi-leaf collimator assembly of claim 1 wherein the first and second multi-leaf collimators are permanently mounted to a linear accelerator.

9. The multi-leaf collimator assembly of claim 1 wherein the first and second multi-leaf collimators are removably mounted to a linear accelerator as a single unit.

10. The multi-leaf collimator assembly of claim 1 further comprising a controller for controlling movement of at least one leaf within the first multi-leaf collimator and two or more leaves of the second multi-leaf collimator such that the at least one leaf and the two or more leaves move in concert along a common axis.

11. A linear accelerator system for applying radiation treatment, the system comprising:
a linear accelerator for generating a radiation beam;
a first multi-leaf collimator having multiple leaves movable relative to a source of radiation and defining an aperture through which the radiation beam passes, thereby creating a first radiation beam field, the leaves of the first multi-leaf collimator having a first depth along a radiation beam direction;
a second multi-leaf collimator having multiple leaves movable relative to the source of radiation, the leaves of the second multi-leaf collimator having a second depth along the radiation beam direction, the second depth being less than the first depth and insufficient to fully attenuate the first radiation beam field, wherein at least one leaf of the second multi-leaf collimator intersects a portion of the first radiation beam field to define a second radiation beam field comprising, a first subfield and a second subfield, the second subfield resulting from the intersection of the at least one leaf of the second multi-leaf collimator with the first radiation beam field and having lower intensity than the first subfield.

12. The linear accelerator system of claim 11 wherein the second multi-leaf collimator is positioned apart from and movable relative to the first multi-leaf collimator.

13. The linear accelerator system of claim 12 wherein the second depth is between 20 millimeters and 40 millimeters.

14. The linear accelerator system of claim 12 wherein the second multi-leaf collimator is positioned below the first multi-leaf collimator relative to the linear accelerator.

15. The linear accelerator system of claim 11 wherein each leaf of the first multi-leaf collimator has a first thickness when measured in a direction perpendicular to an axis from the source of radiation to a treatment table wherein each leaf of the second multi-leaf collimator has a second thickness, the second thickness being no greater than half the first thickness.

16. The linear accelerator system of claim 11 wherein the second subfield comprises a penumbra of the first radiation beam field.

17. The linear accelerator system of claim 11 further comprising a controller for controlling movement of at least one leaf within the first multi-leaf collimator and two or more leaves of the second multi-leaf collimator such that the at least one leaf and the two or more leaves move in concert along a common axis.

18. A method of delivering radiation therapy, the method comprising:
defining an aperture by adjusting a positioning of one or more leaves of a first multi-leaf collimator, wherein the one or more leaves of the first multi-leaf collimator have a first depth along a radiation beam direction;
delivering a first radiation beam field through the aperture; and
intersecting a portion of the first radiation beam field with at least one leaf of a second multi-leaf collimator to define a second radiation beam field comprising a first subfield and a second subfield, the at least one leaf of the second multi-leaf collimator having a second depth along the radiation beam direction, the second depth being less than the first depth and insufficient to fully attenuate the first radiation beam field, wherein the second subfield results from the intersection of the at least one leaf of the second multi-leaf collimator with the first radiation beam field and has a lower intensity than the first subfield.

19. The method of claim 18 wherein adjusting the positioning of one or more leaves of the first multi-leaf collimator causes the at least one leaf of the second multi-leaf collimator to move in concert with the one or more leaves of the first multi-leaf collimator.

20. The method of claim 19 wherein an end of at least a first leaf of the second multi-leaf collimator is aligned with an end of the first multi-leaf collimator partially defining the aperture and at least a second leaf of the second multi-leaf collimator extends beyond the end of the first multi-leaf collimator into the first radiation beam field.

* * * * *